US011712351B2

(12) United States Patent
McNicholas et al.

(10) Patent No.: US 11,712,351 B2
(45) Date of Patent: Aug. 1, 2023

(54) SINGLE AXIS ANKLE-FOOT PROSTHESIS WITH MECHANICALLY ADJUSTABLE RANGE OF MOTION

(71) Applicant: UNITED STATES GOVERMENT AS REPRESENTED BY THE DEPARTMENT OF VETERANS AFFAIRS, Washington, DC (US)

(72) Inventors: Sara Koehler McNicholas, Minneapolis, MN (US); Eric Nickel, Minneapolis, MN (US); Stuart Fairhurst, Minneapolis, MN (US); Justin Keister, Minneapolis, MN (US); Andrew H. Hansen, Minneapolis, MN (US)

(73) Assignee: United States Government As Represented By The Department Of Veterans Affairs, Washington, DC (US)

( * ) Notice: Subject to any disclaimer, the term of this patent is extended or adjusted under 35 U.S.C. 154(b) by 324 days.

(21) Appl. No.: 17/251,428

(22) PCT Filed: Jun. 14, 2019

(86) PCT No.: PCT/US2019/037225
§ 371 (c)(1),
(2) Date: Dec. 11, 2020

(87) PCT Pub. No.: WO2019/241654
PCT Pub. Date: Dec. 19, 2019

(65) Prior Publication Data
US 2021/0106442 A1 Apr. 15, 2021

Related U.S. Application Data

(60) Provisional application No. 62/685,103, filed on Jun. 14, 2018.

(51) Int. Cl.
*A61F 2/66* (2006.01)
*A61F 2/70* (2006.01)
(Continued)

(52) U.S. Cl.
CPC .............. *A61F 2/6607* (2013.01); *A61F 2/70* (2013.01); *A61F 2002/5009* (2013.01);
(Continued)

(58) Field of Classification Search
None
See application file for complete search history.

(56) References Cited

U.S. PATENT DOCUMENTS

| 92,031 A | 6/1869 | Foster |
| 2,617,115 A | 11/1952 | Ellery |

(Continued)

FOREIGN PATENT DOCUMENTS

| DE | 1 211 354 | * | 2/1966 | ............... A61F 2/66 |
| FR | 2 653 327 A1 | * | 4/1991 | ........... A61F 2/6607 |
| SE | 456 134 B | * | 9/1988 | ........... A61F 2/6607 |

OTHER PUBLICATIONS

Search Report and Written Opinion of corresponding PCT Application No. PCT/US2019/037225, dated Sep. 12, 2019.
(Continued)

*Primary Examiner* — David H Willse
(74) *Attorney, Agent, or Firm* — Ballard Spahr LLP

(57) ABSTRACT

An ankle prosthesis can have a base and an upper hinge component that is pivotably attached to the base about an axis. First and second biasing elements can bias the upper hinge component in first and second rotational directions, respectively. At least one selectively extendable and retractable locking element can extend from one of the base and the upper hinge component and engage the other of the base and
(Continued)

the upper hinge component to limit the pivotable movement of the upper hinge component.

18 Claims, 13 Drawing Sheets

(51) Int. Cl.
*A61F 2/76* (2006.01)
*A61F 2/50* (2006.01)
*A61F 2/68* (2006.01)
(52) U.S. Cl.
CPC .......... *A61F 2002/5018* (2013.01); *A61F 2002/5038* (2013.01); *A61F 2002/5043* (2013.01); *A61F 2002/6614* (2013.01); *A61F 2002/6854* (2013.01); *A61F 2002/701* (2013.01); *A61F 2002/762* (2013.01); *A61F 2002/769* (2013.01); *A61F 2002/7625* (2013.01)

(56) References Cited

U.S. PATENT DOCUMENTS

| | | | |
|---|---|---|---|
| 4,499,613 A * | 2/1985 | Yarrow | ............... A61F 2/6607 623/48 |
| 4,777,941 A | 10/1988 | Borig | |
| 5,766,264 A | 6/1998 | Lundt | |
| 2010/0030343 A1 | 2/2010 | Hansen | |
| 2012/0130508 A1 | 5/2012 | Harris et al. | |
| 2013/0144402 A1 | 6/2013 | Clausen et al. | |
| 2014/0249652 A1 | 9/2014 | Taszreak | |
| 2017/0325974 A1 | 11/2017 | Lincoln et al. | |
| 2018/0036149 A1 | 2/2018 | Harris et al. | |

OTHER PUBLICATIONS

Examination Report for corresponding EPO application No. EP 19 81 9396, dated Feb. 7, 2022.

* cited by examiner

SINGLE AXIS ANKLE-FOOT PROSTHESIS WITH MECHANICALLY ADJUSTABLE RANGE OF MOTION

CROSS REFERENCE TO RELATED APPLICATIONS

This is a U.S. National Phase Application of International Application No. PCT/US2019/037225, filed Jun. 14, 2019, which claims priority to and the benefit of the filing date of U.S. Provisional Application No. 62/685,103, filed Jun. 14, 2018, the contents of which are incorporated herein by reference in their entirety.

FIELD

The disclosed invention relates to ankle prostheses and more particularly, to ankle prostheses that provide an adjustable range of motion.

BACKGROUND

Prosthetic ankle-foot systems are primarily designed for walking mobility. Conventional systems do not provide for adjustable stability, which can be particularly desirable during initial rehabilitation phases after an amputation.

SUMMARY

Described herein, in various aspects, is an ankle prosthesis. The ankle prosthesis can include a base, an upper hinge component, first and second biasing elements, and a first selectively extendable and retractable locking element. The upper hinge component can be pivotably attached to the base about an axis. The first biasing element can be configured to bias the upper hinge component in a first rotational direction and toward a neutral position. The second biasing element can be configured to bias the upper hinge component in a second rotational direction that is opposite the first rotational direction and toward the neutral position. The first selectively extendable and retractable locking element can be selectively extendable (axially advanced) to a locking position. The first selectively extendable locking element can extend from one of the base and the upper hinge component. When the upper hinge component is in the neutral position and the first selectively extendable and retractable locking element is in the locking position, the first selectively extendable and retractable locking element can engage the other of the base and the upper hinge component.

In use, the first selectively extendable and retractable locking element can be selectively retractable from the locking position to disengage said other of the base and the upper hinge component to permit movement of the upper hinge component in the first rotational direction from the neutral position.

Optionally, the ankle prosthesis can further comprise a second selectively extendable and retractable locking element that is selectively extendable to a locking position. The second selectively extendable locking element can extend from one of the base and the upper hinge component. When the upper hinge component is in the neutral position and the second selectively extendable and retractable locking element is in the locking position, the second selectively extendable and retractable locking element can engage the other of the base and the upper hinge component.

In use, the second selectively extendable and retractable locking element can be selectively retractable from the locking position to disengage said other of the base and the upper hinge component to permit movement of the upper hinge component in the second rotational direction from the neutral position.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

These and other features of the preferred embodiments of the invention will become more apparent in the detailed description in which reference is made to the appended drawings wherein.

DETAILED DESCRIPTION

Figure 1:
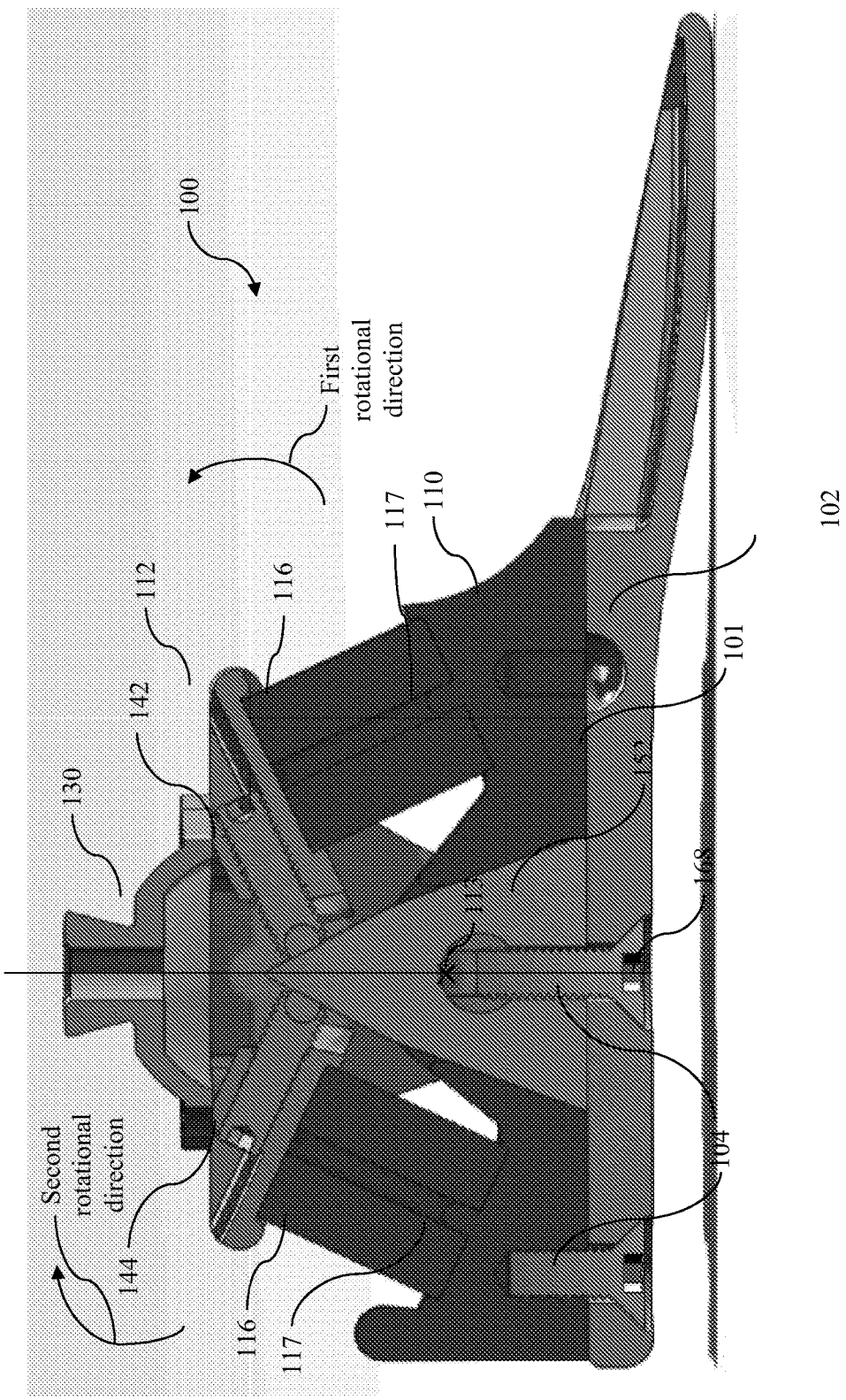
FIG. 1 is cross sectional view of an ankle prosthesis in accordance with embodiments disclosed herein.

The present invention now will be described more fully hereinafter with reference to the accompanying drawings, in which some, but not all embodiments of the invention, are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a," "an," and "the" include plural referents unless the context clearly dictates otherwise. For example, use of the term "a screw" can refer to one or more of such screws, and so forth.

All technical and scientific terms used herein have the same meaning as commonly understood to one of ordinary skill in the art to which this invention belongs unless clearly indicated otherwise.

As used herein, the terms "optional" or "optionally" mean that the subsequently described event or circumstance may or may not occur, and that the description includes instances where said event or circumstance occurs and instances where it does not.

As used herein, the term "at least one of" is intended to be synonymous with "one or more of." For example, "at least one of A, B and C" explicitly includes only A, only B, only C, and combinations of each.

The word "or" as used herein means any one member of a particular list and also includes any combination of members of that list.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Optionally, in some aspects, when values are approximated by use of the antecedent "about," it is contemplated that values within up to 15%, up to 10%, up to 5%, or up to 1% (above or below) of the particularly stated value can be included within the scope of those aspects. Similarly, in some aspects, when values or characteristics are approximated by the use of the antecedent "approximately," "generally," or "substantially," it is contemplated that values within up to 15%, up to 10%, up to 5%, or up to 1% (above or below) of the particularly stated value or characteristic can be included within the scope of those aspects.

The following description supplies specific details in order to provide a thorough understanding. Nevertheless, the skilled artisan would understand that the apparatus, system, and associated methods of using the apparatus can be implemented and used without employing these specific details. Indeed, the apparatus, system, and associated methods can be placed into practice by modifying the illustrated apparatus, system, and associated methods and can be used in conjunction with any other apparatus and techniques conventionally used in the industry.

Figure 2:
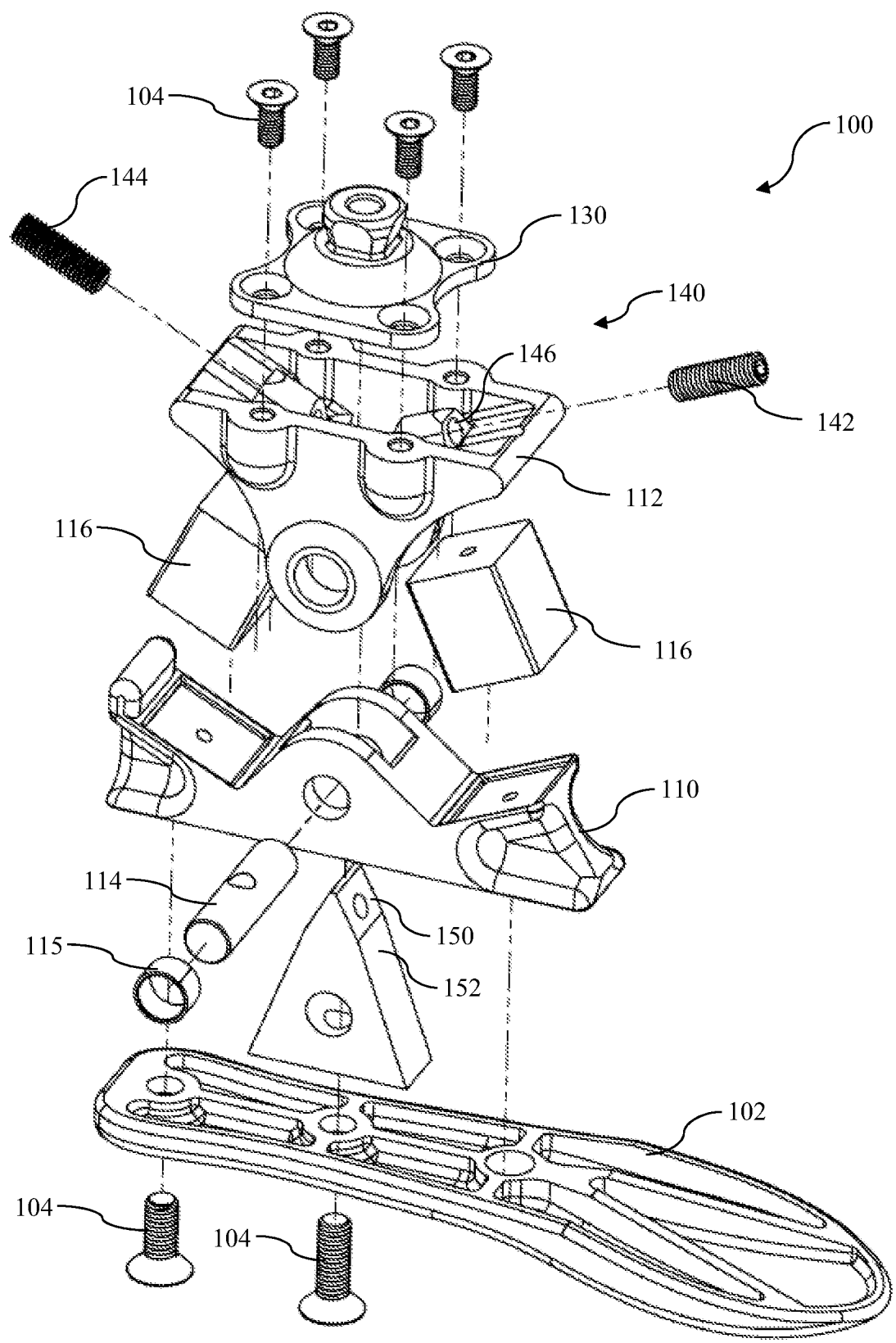
FIG. 2 is an exploded view of the ankle prosthesis of FIG. 1.
Figure 3:
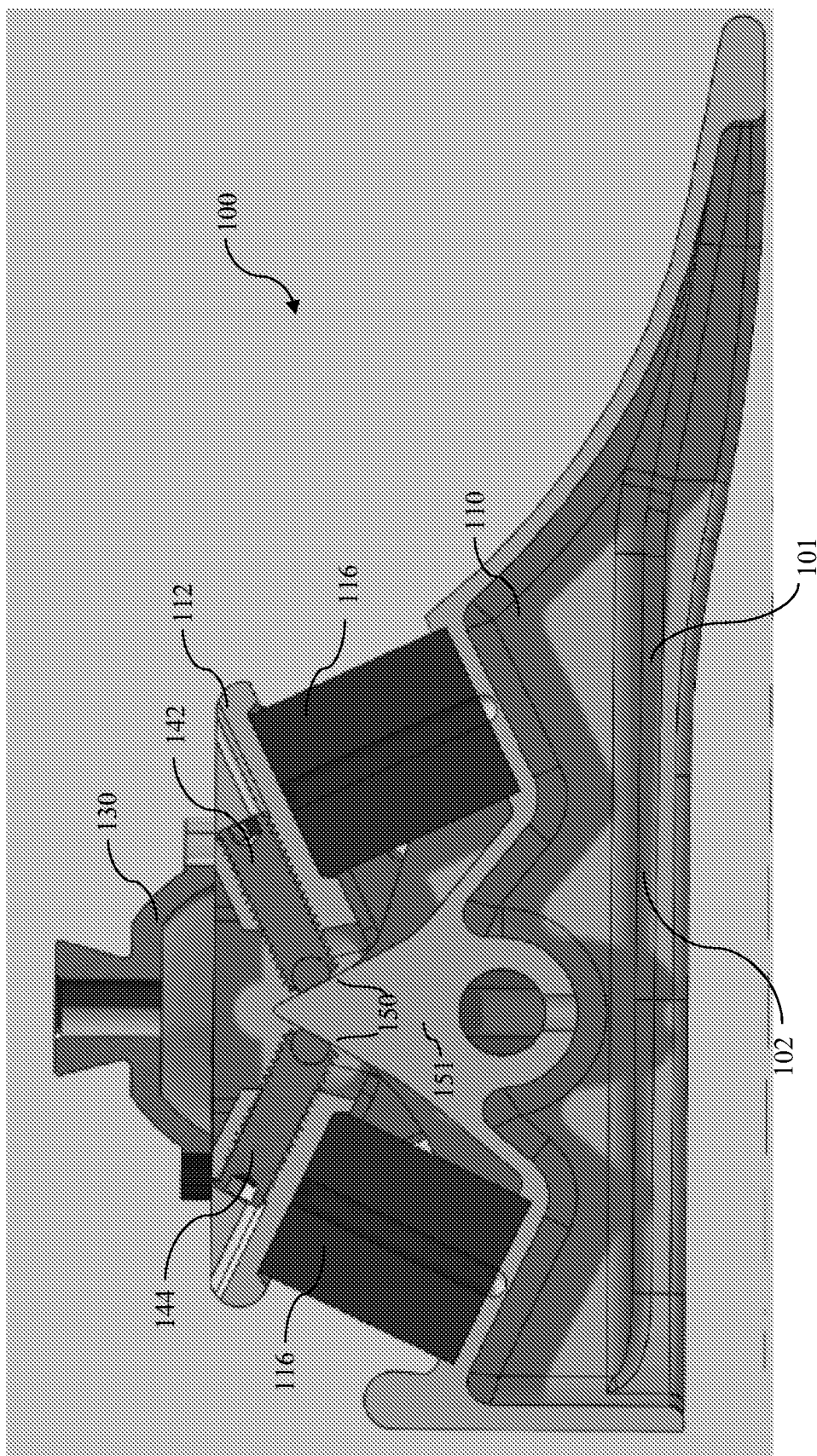
FIG. 3 is a cross sectional view of another embodiment of an ankle prosthesis in accordance with embodiments disclosed herein.
Figure 4:
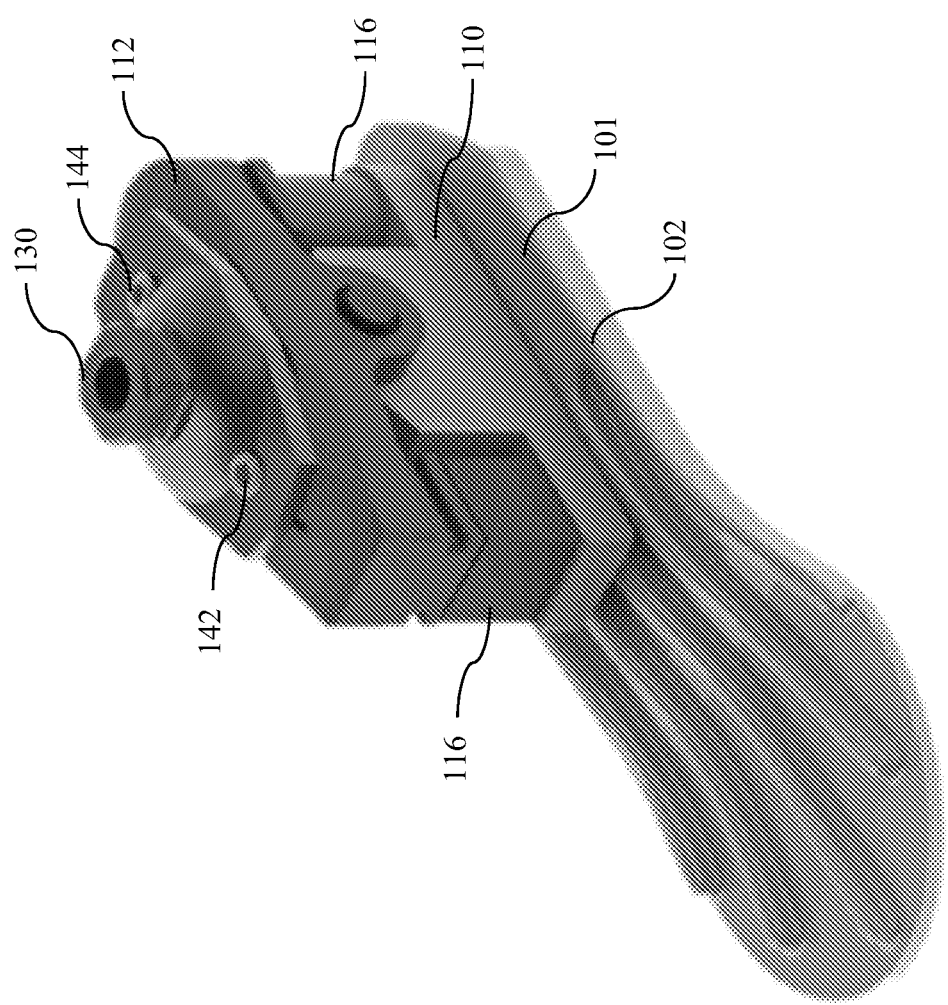
FIG. 4 is a perspective view of yet another embodiment of an ankle prosthesis in accordance with embodiments disclosed herein.

Disclosed herein, in various aspects and with reference to FIGS. 1 and 2, is an ankle prosthesis 100. The ankle prosthesis 100 can comprise a footplate 102. The footplate 102 can have high stiffness. The footplate 102 can have high stiffness, high strength, and low weight. Exemplary materials for the footplate include metals (e.g., titanium), metal alloys (e.g., titanium alloys), and composite materials as are known in the art. The footplate 102 can have a contour that is configured to be received in a prosthetic foot shell (i.e., in a receptacle defined within a prosthetic foot as is known in the art. Following receipt of the footplate 102 within the prosthetic foot, it is contemplated that outer surfaces of the footplate 102 can engage or be coupled or secured to interior surfaces of the prosthetic foot to securely position the footplate within the prosthetic foot. A lower hinge component 110 can attach to the footplate 102 via mounting hardware (e.g., screws 104) to define at least a portion of a base 101. In further embodiments (e.g., as shown in FIG. 3), the lower hinge component 110 can attach to the footplate 102 via unitary construction (i.e., the lower hinge component 110 and the footplate 102 can be formed as a single (one-piece), monolithic component). Accordingly, the base 101 can comprise the lower hinge component 110 and footplate 102 as a unitary body. An upper hinge component 112 can pivotably attach to the lower hinge component 110 about an axis 113 via a pivot pin 114 and journal bearings 115. A pair of spring-like viscoelastic rubber bumpers 116 can securely couple or attach to the lower hinge component, one on each side of the pivot pin 114. A respective (e.g., lower) surface of the upper hinge component 112 can engage each of the bumpers 116 so that as the respective surface compresses a respective bumper 116, the respective bumper 116 provides a reactionary spring force to bias the upper hinge component 112 toward a neutral position. The neutral position can be a position to which, under no outside force, the upper hinge component 112 moves. In this way, the bumpers 116 can store energy and provide resistance to ankle prosthesis flexion. In some embodiments (e.g., FIG. 4), the anterior bumper 116 can be rounded to fit inside a foot shell (i.e., a receptacle within a prosthetic foot). Optionally, the bumpers 116 can receive, and be positioned on, pegs 117 that extend from the lower hinge component 110. In further embodiments, springs or various other elastic components can be used to bias the upper component 112 toward the neutral position. A pyramid connector 130 can attach to the upper hinge component 112 via screws 104. As known to those skilled in the art, the pyramid connector 130 can have an inverted pyramid portion (tapering in a downward direction) that is configured to engage four set screws. Said set screws enable a therapist to adjust the rotational orientation of the prosthesis with respect to an appendage of a user (e.g., a subject or patient).

The ankle prosthesis 100 can comprise an adjustable range limiting system 140. The adjustable range limiting system 140 can include a first adjustment screw 142 and a second adjustment screw 144. In some embodiments, the first and second adjustment screws 142, 144 can comprise set screws. Each of the first adjustment screw 142 and the second adjustment screw 144 can travel in a respective threaded hole 146 within the upper hinge component 112. The position of each of the first and second adjustment screws 142, 144 can be adjusted along a respective axis so that a respective distal end can extend from the upper hinge component 112 by a select distance. The distal end of each screw can be positioned to engage a respective stop surface 150. As shown in FIG. 3, in some embodiments, the stop surfaces 150 can be surfaces of a protrusion 151 extending from the base 101. As shown in FIGS. 1 and 2, in further embodiments, the stop surfaces can be surfaces of a separate stop surface component 152 that is attached to the footplate 102 via a screw 104 so that the stop surfaces 150 are rotationally fixed to (i.e., cannot rotate with respect to) the lower hinge component 110. Thus, the base 101 can further comprise the stop surface component 152.

Figure 6:
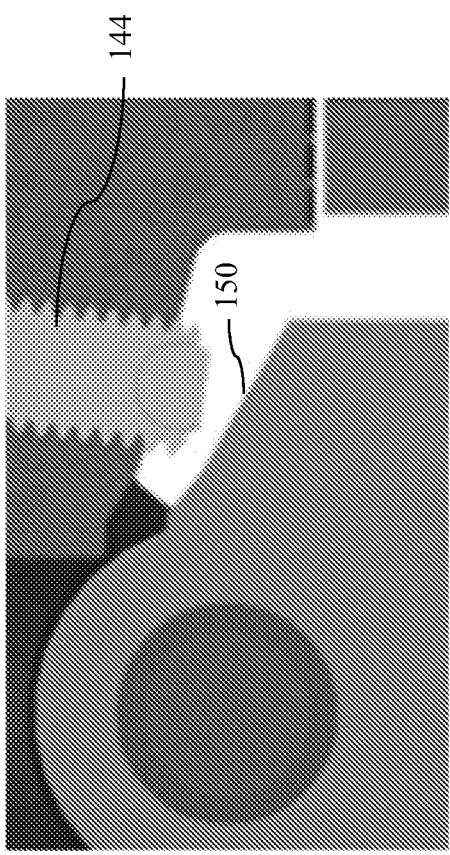
FIG. 6 is a partial cross sectional view of the ankle prosthesis of FIG. 4, with an adjustment screw in a first position.
Figure 7:
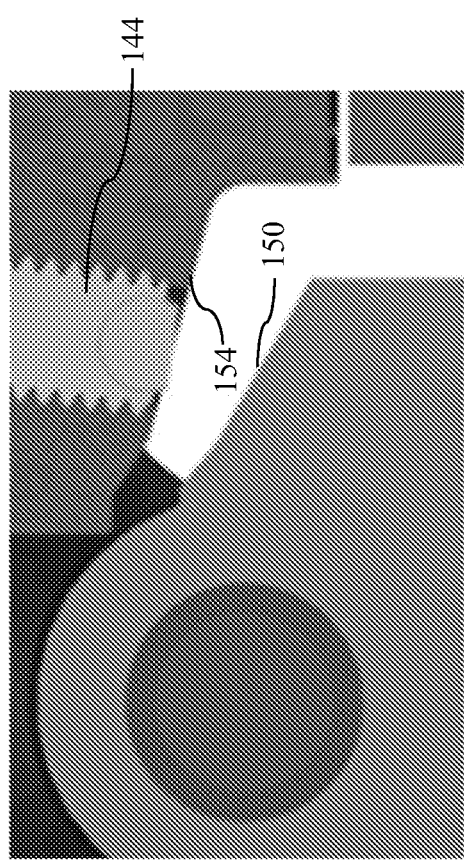
FIG. 7 is a partial cross sectional view of the ankle prosthesis of FIG. 4, with the adjustment screw in a second position.

In this way, the first and second adjustment screws 142, 144 can be set at various positions so that the distal ends of the screws engage respective stop surfaces 150 when the upper and lower hinge components 110, 112 are disposed at select angles with respect to each other. Accordingly, the first and second adjustment screws 142, 144 can limit the pivotal range of motion of the upper hinge component 112 with respect to the lower hinge component 110 in respective first and second directions. For example, as shown in FIGS. 1 and 3, both of the first and second screws can be set in respective locking positions (with the screws fully advanced within the threaded holes) so that the ankle prosthesis 100 is locked and does not allow any pivotal movement between the upper and lower hinge components 110, 112. The first adjustment screw 142 can be retracted or backed away from its locking position to disengage a stop surface and allow varying degrees of dorsiflexion in the ankle prosthesis 100. Similarly, the second adjustment screw 144 can be retracted or loosened from its locking position to disengage a stop surface and allow varying degrees of plantar flexion in the ankle prosthesis 100. For example, FIG. 6 illustrates the second set screw 144 in a position allowing for partial plantar flexion. FIG. 7 illustrates the second set screw 144 in a fully open position that allows for a maximum plantar flexion range of mobility. That is, during flexion, the stop surface 150 can engage a lower surface 154 of the upper hinge component 112 instead of the second set screw 144, with the engagement between the stop surface and the lower surface of the upper hinge component defining a limit on the range of motion of the upper hinge component. As shown, the first and second adjustment screws 142, 144 can be disposed on opposite sides of a vertical plane 168 that includes the axis 113. In some embodiments, the maximum range of motion for plantar flexion can be fifteen degrees from the neutral position in the first direction, and the maximum range of motion for the dorsiflexion can be fifteen degrees from the neutral position in the second direction. In various further embodiments, the maximum range of motion in each of the first and second directions can be twenty degrees, or twenty five degrees, or more. These ranges of motion can be particularly desirable in situations where it is necessary to challenge a user (e.g., a patient). During normal walking, people typically use about ten to fifteen degrees of plantar flexion and eight to twelve degrees of dorsiflexion. Accordingly, it is contemplated that the set range of motion in the dorsiflexion direction can be different from the set range of motion in the plantar flexion direction. For example, the range of motion can be set to ten degrees of plantar flexion and eight degrees of dorsiflexion.

Exemplary configurations of the first and second directions are depicted in the figures. However, it is contemplated that, depending on the specific structure of the described ankle prostheses, the depicted first and second directions can be inverted (with the first direction corresponding to second direction as depicted, and the second direction corresponding to the first direction as depicted).

It should be understood that positions of the first and second adjustment screws 142, 144 are not limited to holes within the upper hinge component 112. For example, in further embodiments, the first and second adjustment screws 142, 144 can extend from the lower hinge component 110 and selectively engage or disengage stop surfaces of the upper hinge component 112 to control the permitted range of motion of the upper hinge component.

Figure 13:
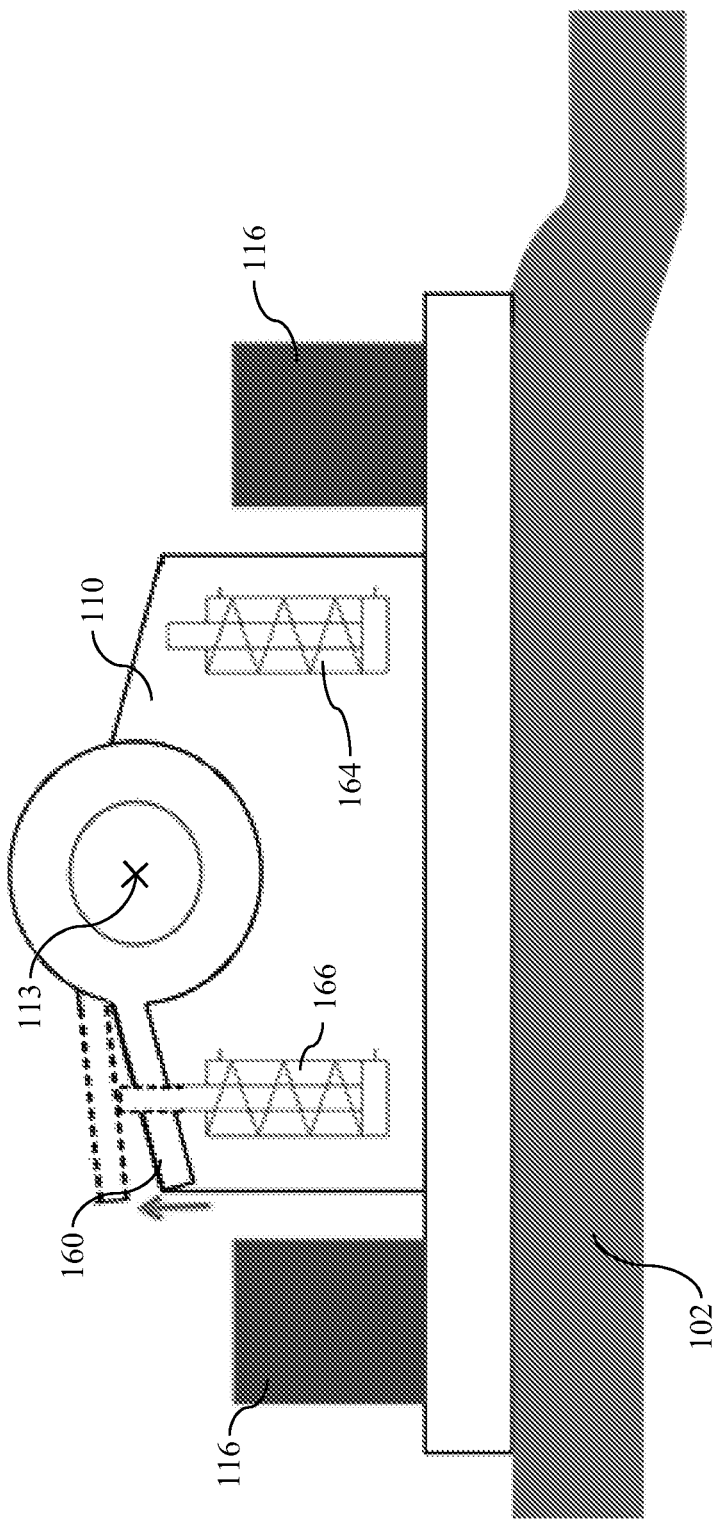
FIG. 13 is a schematic of an embodiment of an electronically actuated ankle prosthesis in accordance with embodiments disclosed herein.

Referring to FIG. 13, in a further embodiment, the adjustable range limiting system 140 can be electronically controlled. The lower hinge component can have receiver surfaces 160 (one shown) that are pivotable about the axis 113 and are configured to engage lower surfaces of the upper hinge component 112 (FIG. 1) after a select relative pivotal rotation. A pair of non-backdrivable linear actuators 164, 166 can be disposed in the lower hinge component 110. The linear actuators 164, 166 can independently position respective receiver surfaces 160 to engage the lower surfaces of the upper hinge component 112 at select pivotal angles (for example, within the ranges described herein), thereby limiting the pivotal movement of the upper hinge component 112 and, therefore, the pivotal movement of the ankle prosthesis 100.

Figure 14:
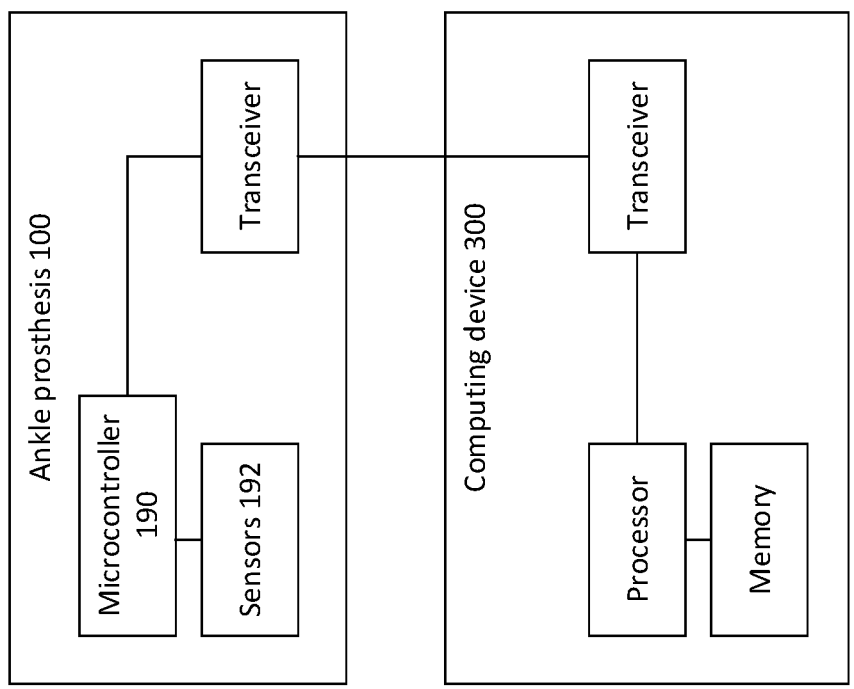
FIG. 14 illustrates a block diagram of a system for electronically controlling the ankle prosthesis of FIG. 13.

Referring also to FIG. 14, in some embodiments, the ankle prosthesis 100 can comprise a microcontroller 190 that can control the linear actuators 164, 166. The ankle prosthesis 100 can further comprise sensors 192 (e.g., accelerometers) that can provide feedback to the microcontroller. The microcontroller, in cooperation with feedback from the sensors 192 can automate control of the range of motion of the prosthesis. In some embodiments, the ankle prosthesis 100 can connect to a remote computing device 300, such as a smartphone or tablet, through means such as Bluetooth or other low energy communication transceiver protocol. In this way, a therapist can electronically adjust the allowable range of motion in the ankle prosthesis 100.

Figure 5:
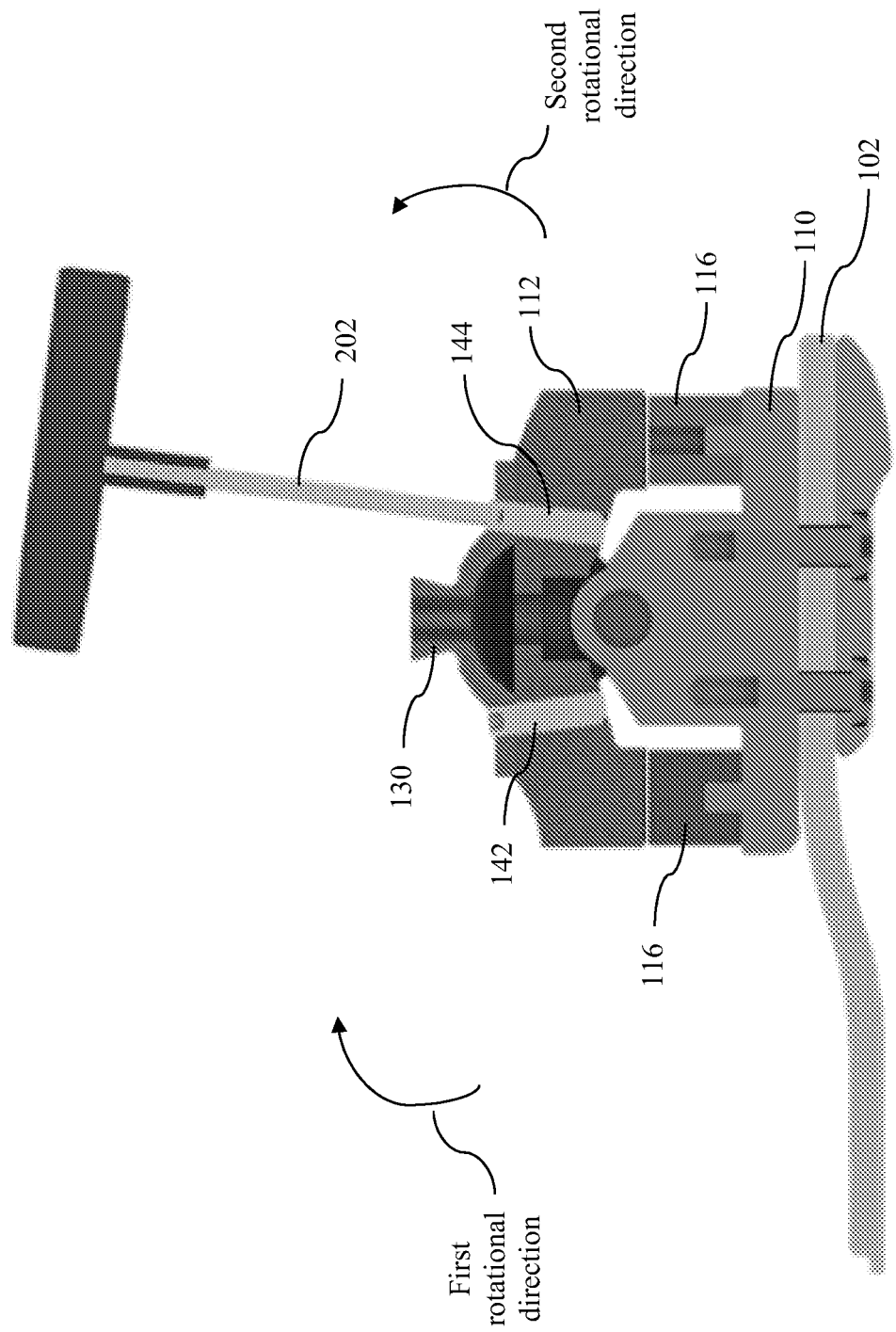
FIG. 5 is a cross sectional view of the ankle prosthesis of FIG. 4.
Figure 8:
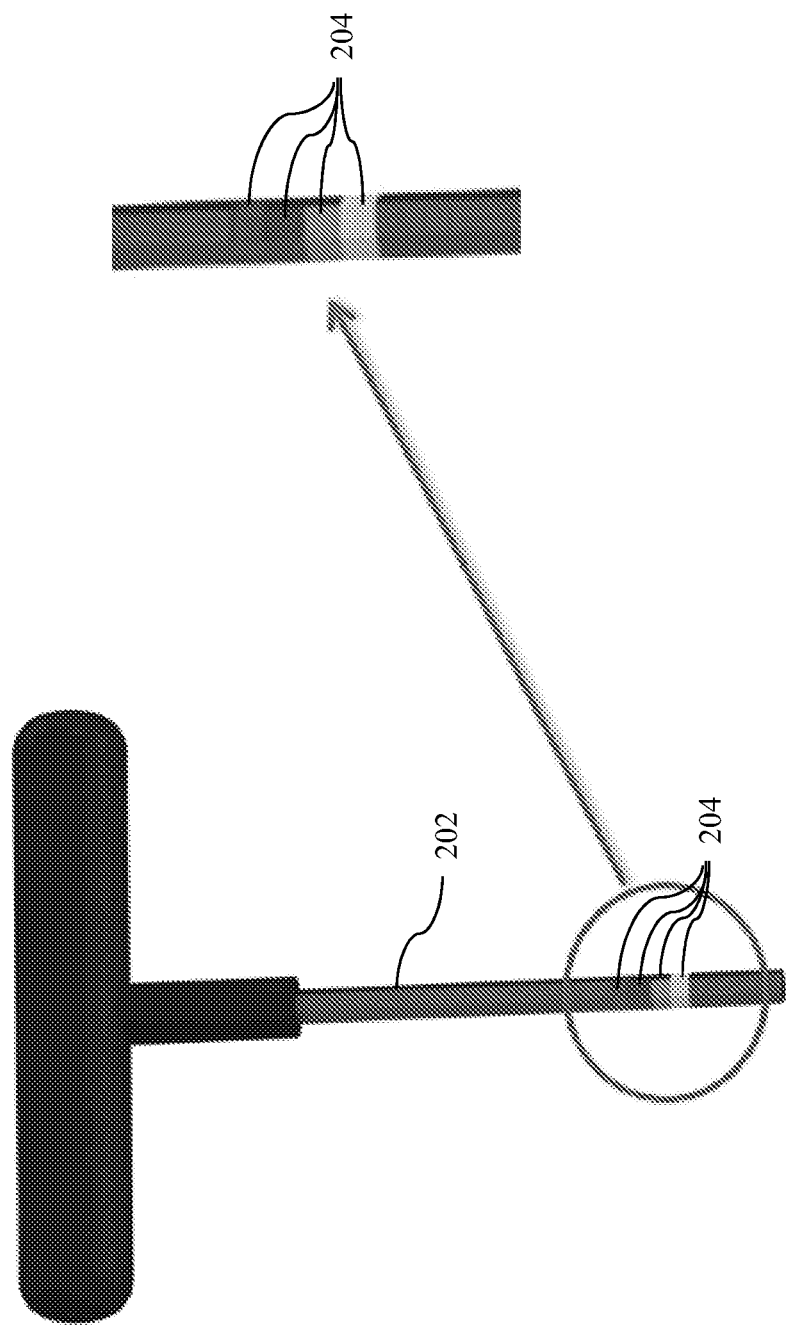
FIG. 8 is a side view of an adjustment wrench for use with the ankle prosthesis of FIG. 5.

The ankle prosthesis can comprise a range indicator that indicates the extent to which the ankle prosthesis 100 can bend from the neutral position in a given angular direction, or the ankle prosthesis' range of motion. Referring to FIGS. 5 and 8, according to a first embodiment of the range indicator, the first and second adjustment screws 142, 144 can be adjustable by a hex wrench 202. The hex wrench 202 can have markings 204. When the hex wrench 202 is inserted into an adjustment screw (e.g., the first adjustment screw 142 or the second adjustment screw 144), a portion of the hex wrench 202 can be covered by the respective threaded hole 146 into which it is inserted (and not visible). The markings 204 that are visible (i.e., the markings that are not within the threaded hole 146 and covered by the upper hinge component) can indicate the maximum angle or angle range to which the ankle prosthesis can be pivoted (bent). For example, a visible red band can indicate a range of zero degrees to five degrees of allowable range of motion, a visible red and blue band can indicate a range of five degrees to ten degrees of allowable range of motion, etc.

Figure 9:
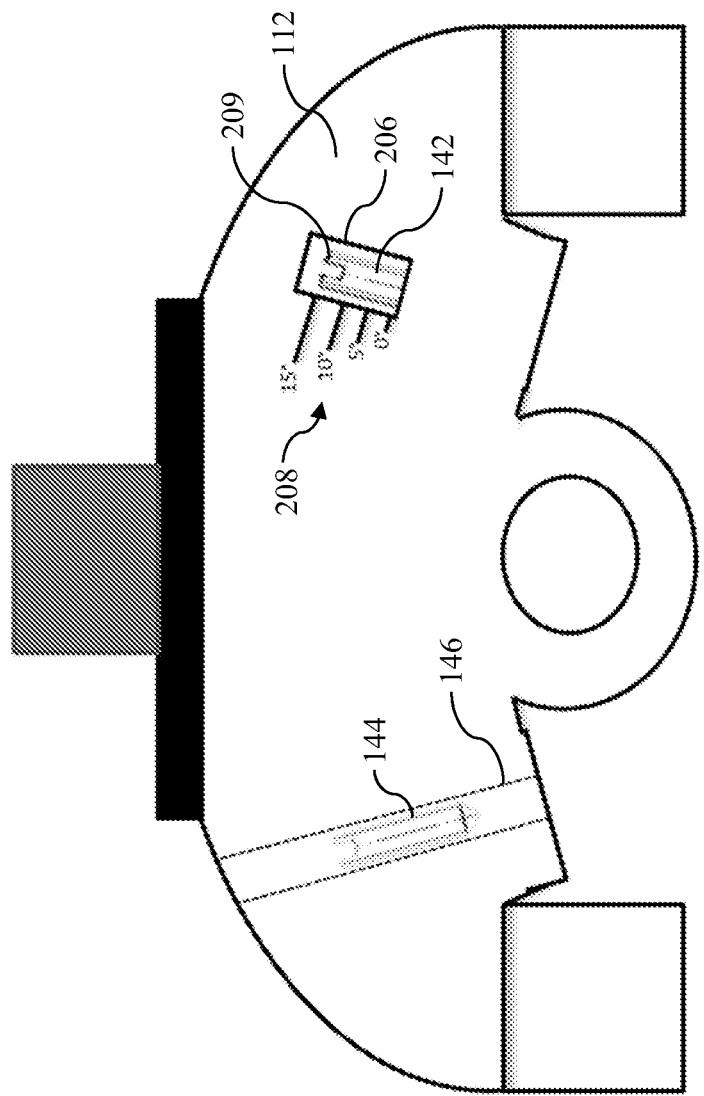
FIG. 9 is a schematic of a portion of the ankle prosthesis of FIG. 4 having an embodiment of a range indicator.

Referring to FIGS. 5 and 9, in a second embodiment of the range indicator, the upper hinge component 112 can define a window 206 (e.g., a hole that extends from an outer surface of the upper hinge component 112 to the threaded holes 146) along each threaded hole 146 that can show the position of the adjustment screw within the threaded hole. Depending on where a back end of the respective adjustment screw lies within the window 206, the ankle prosthesis' range of motion can be determined. In some embodiments, markings 208 proximate the window 206 can indicate the range of motion for the ankle when the back end 209 of the respective adjustment screw is aligned with each said marking 208.

In a third embodiment of the range indicator, the pitch of each adjustment screw can be known so that each turn can change the range of motion by a known amount. The pitch can be selected so that the range of motion changes by a desired amount for every screw rotation.

Figure 10:
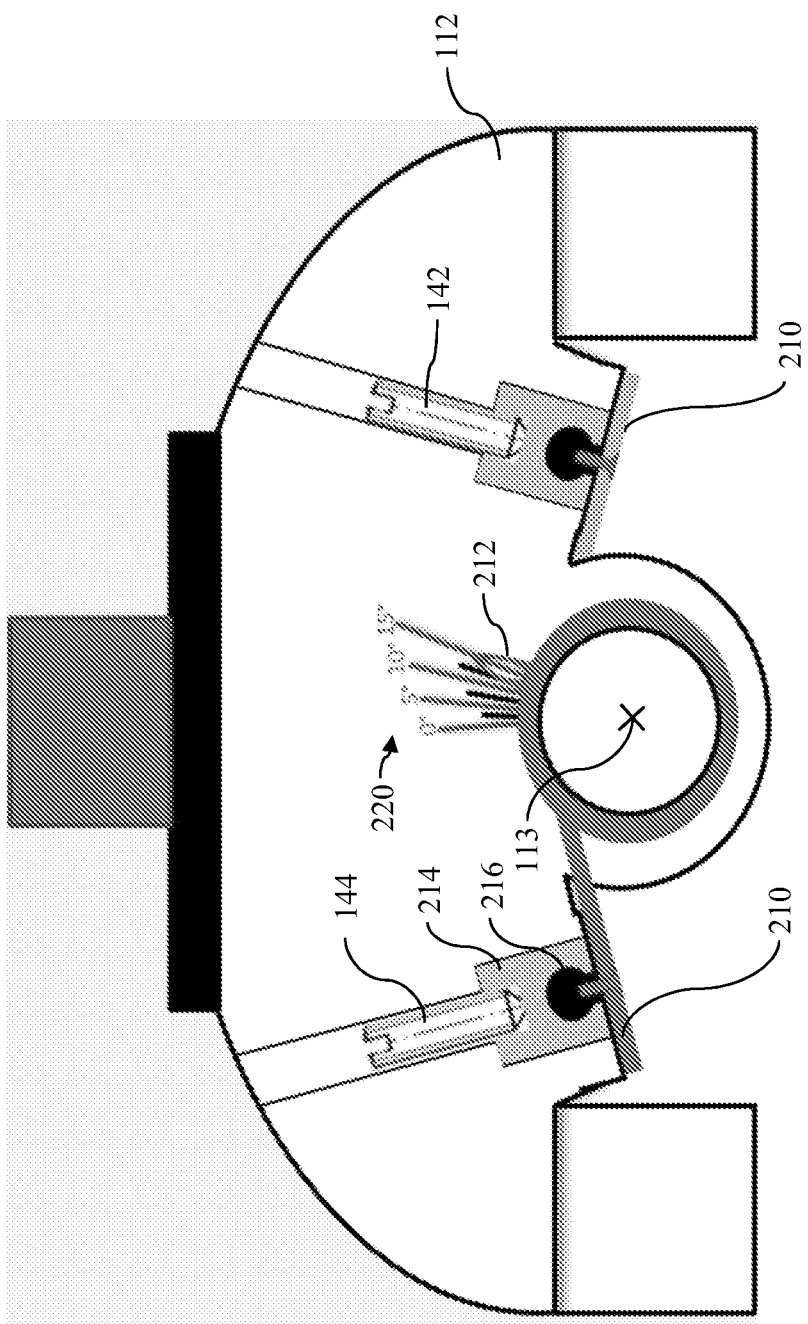
FIG. 10 is a schematic of a portion of the ankle prosthesis of FIG. 4 having another embodiment of a range indicator.

Referring to FIG. 10, in a fourth embodiment of the indicator, a pair of metal structures 210 having respective pointers 212 (one shown) attached thereto are pivotably attached about the axis 113 to the ankle prosthesis 100. The metal structures 210 can be coupled or attached to respective adjustment screws 142, 144. For example, each adjustment screw 142, 144 can screw into a cap 214, and the cap 214 can, in turn, attach via a ball joint 216 to a respective metal structure 210 to thereby enable rotational movement between the adjustment screw 142, 144 and the respective metal structure 210. Instead of the adjustment screws engaging the stop surfaces 150 (FIG. 7), lower surfaces of the metal structures 210 can engage the respective stop surfaces 150. As each adjustment screw 142, 144 is positioned, the respective metal structure 210 and pointer 212 is accordingly rotationally adjusted. For example, as the second adjustment screw 144 moves downward, the metal structure 210 can rotate counter-clockwise, thereby indicating a decreasing plantar flexion range of motion. Each pointer 212 can point to a marker 220 (e.g., a marker on the upper hinge portion 112) at a point that can vary based on the position of the respective adjustment screw.

Figure 11:
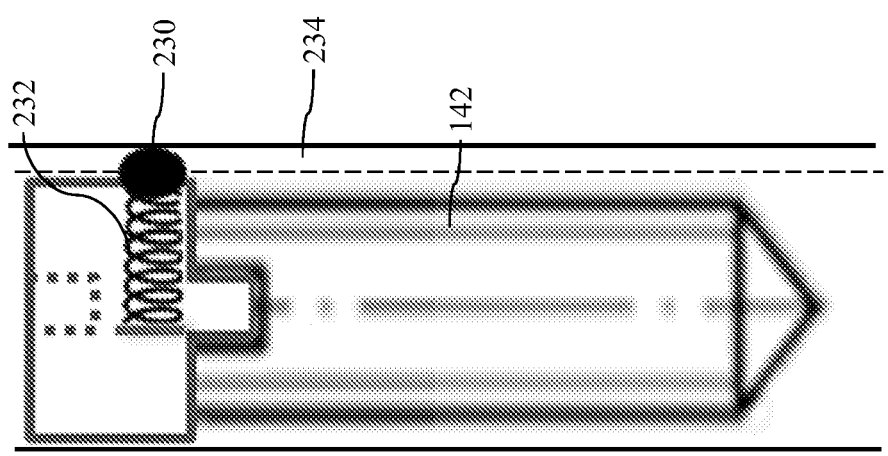
FIG. 11 is a set screw for use with the ankle prosthesis of FIG. 1.

Referring to FIG. 11, in a fifth embodiment of the range indicator, the adjustment screws (screw 142 shown) can each comprise a ball 230 biased radially outward via a spring 232. The ball 230 can be received into one or a plurality of receptacles along the length of travel of the respective adjustment screw and oriented perpendicularly to its direction of travel. For example, in one embodiment, the receptacle can comprise a longitudinal groove 234 so that the ball 230 can move into the groove once per rotation. As the spring-loaded ball 230 aligns with a given receptacle, the ball can be received therein to thereby provide an audible click as well as provide a force that the user can feel. Movement into and out of receptacles can correspond to known changes in the position of the adjustment screw and, thus, the ankle prosthesis' range of motion.

Figure 12:
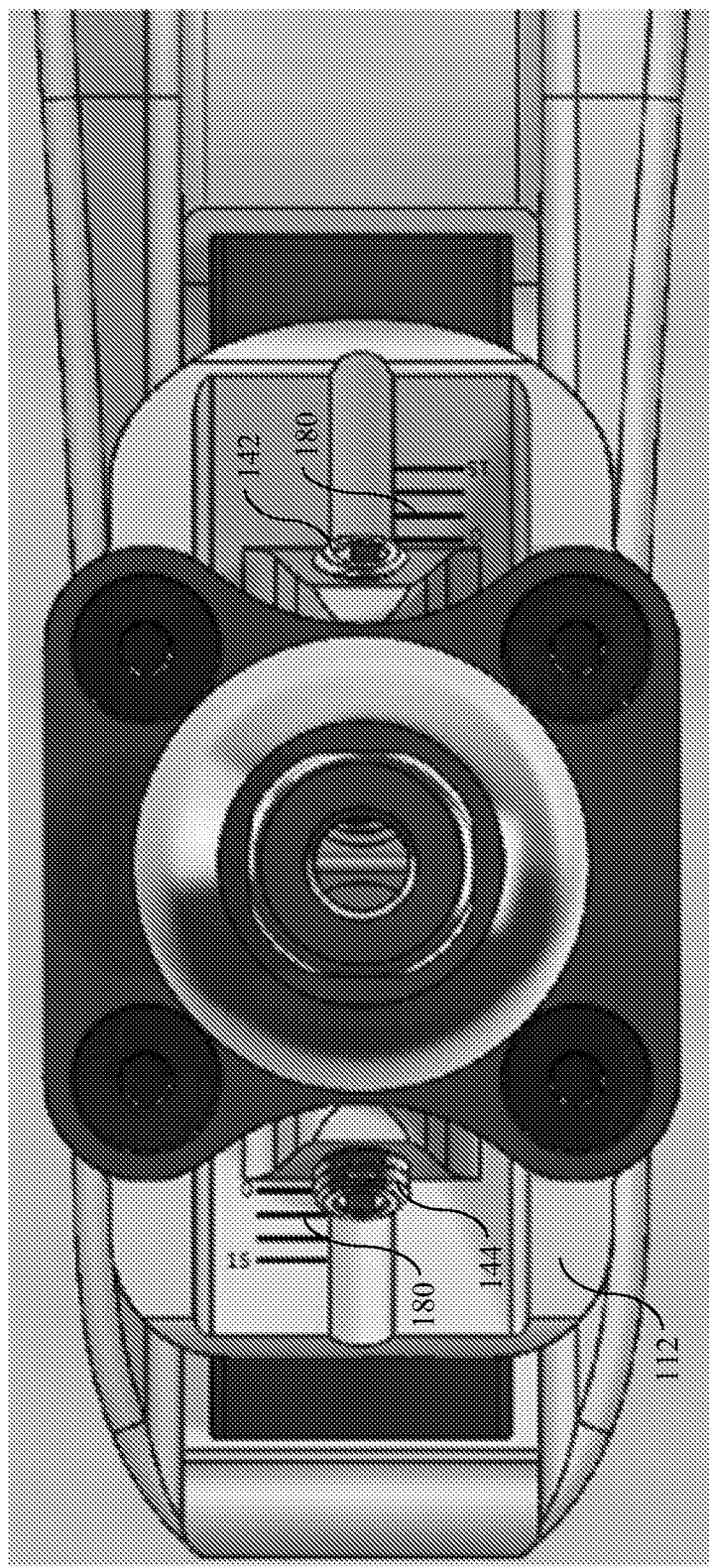
FIG. 12 is a top view of a portion of the ankle prosthesis of FIG. 1 having still another embodiment of a range indicator.

Referring to FIG. 12, according to a sixth embodiment of the range indicator, the upper hinge component 112 can comprise markings 180 that correspond to range of motion limits (e.g. zero to fifteen degrees in increments of five degrees). A back end of each adjustment screw 142, 144 (i.e., the end of the screw configured to receive the adjustment wrench), can extend from the respective hole 146 and align with one of the markings. The marking with which respective back ends of each adjustment screw 142, 144 align can indicate the range of motion in each respective rotational direction. For example, in the illustrated example in FIG. 12, the range indicator indicates that the ankle prosthesis has a range of motion of about two degrees in the dorsiflexion direction and about five degrees in the plantar flexion direction.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: An ankle prosthesis comprising: a base; an upper hinge component that is pivotably attached to the base about an axis; a first biasing element that is configured to bias the upper hinge component in a first rotational direction and toward a neutral position; a second biasing element that is configured to bias the upper hinge component in a second rotational direction that is opposite the first rotational direction and toward the neutral position; and a first selectively extendable and retractable locking element that is selectively extendable to a locking position, wherein the first selectively extendable locking element extends from one of the base and the upper hinge component and, when the upper hinge component is in the neutral position and the first selectively extendable and retractable locking element is in the locking position, the first selectively extendable and retractable locking element engages the other of the base and the upper hinge component.

Aspect 2: The ankle prosthesis of aspect 1, wherein the first selectively extendable and retractable locking element is selectively retractable from the locking position to permit movement of the upper hinge component in the first rotational direction from the neutral position.

Aspect 3: The ankle prosthesis of aspect 2, further comprising a second selectively extendable and retractable locking element that is selectively extendable to a locking position, wherein the second selectively extendable locking element extends from one of the base and the upper hinge component and, when the upper hinge component is in the neutral position and the second selectively extendable and retractable locking element is in the locking position, the second selectively extendable and retractable locking element engages the other of the base and the upper hinge component.

Aspect 4: The ankle prosthesis of aspect 3, wherein the second selectively extendable and retractable locking element is selectively retractable from the locking position to permit movement of the upper hinge component in the second rotational direction from the neutral position.

Aspect 5: The ankle prosthesis of aspect 4, wherein the upper hinge component defines a first threaded hole and a second threaded hole, wherein the first selectively extendable and retractable locking element comprises a first screw disposed within the first threaded hole, wherein the second selectively extendable and retractable locking element comprises a second screw disposed in the second threaded hole, wherein the base defines a first stop surface and a second stop surface, wherein the first screw is configured for advancement along the threaded hole to engage the first stop surface after a first select rotational displacement between the upper hinge component and the base in the first rotational direction to thereby limit a first range of motion that the upper hinge component can pivot with respect to the base in the first rotational direction from the neutral position, wherein the second screw is configured for advancement along the threaded hole to engage the second stop surface after a second select rotational displacement between the upper hinge component and the base in the second rotational direction to thereby limit a second range of motion that the upper hinge component can pivot with respect to the base in the second rotational direction from the neutral position.

Aspect 6: The ankle prosthesis of aspect 4 or aspect 5, wherein the first and second selectively extendable and retractable locking elements are on opposite sides of a vertical plane that includes the axis.

Aspect 7: The ankle prosthesis of aspect 5 or aspect 6, further comprising a range indicator that is configured to indicate the first range of motion and the second range of motion respectively allowed by each of the first and second selectively extendable and retractable locking elements.

Aspect 8: The ankle prosthesis of aspect 7, further comprising an adjustment wrench, wherein the range indicator includes markings on the adjustment wrench, wherein the markings are positioned so that when the adjustment wrench is inserted into one of the first screw and the second screw, the markings that are visible on the adjustment wrench indicate a respective range of motion allowed by said one of the first screw and the second screw.

Aspect 9: The ankle prosthesis of aspect 7, wherein the range indicator comprises a first window along the first threaded hole, wherein the first window is configured to show a position of an end of the first screw, and wherein the range indicator further comprises markings that indicate the first range of motion based on a relationship between the markings and the position of the end of the first screw.

Aspect 10: The ankle prosthesis of aspect 7, wherein the range indicator comprises a gauge comprising a plurality of markers on the upper hinge component and an indicator component that is attached to the first screw and pivotable about the axis, wherein the indicator component further comprises a pointer that rotates as the first screw moves to indicate the first range of motion on the gauge.

Aspect 11: The ankle prosthesis of aspect 7, wherein the range indicator comprises a spring-loaded ball attached to the first screw, wherein the upper hinge component defines at least one cavity that is sized and positioned to receive the ball.

Aspect 12: The ankle prosthesis of aspect 7, wherein the range indicator comprises a first set of markings on the upper hinge component that are positioned with respect to the first screw so that a marking of the first set of markings that is aligned with an end of the first screw indicates the first range of motion.

Aspect 13: The ankle prosthesis of aspect 12, wherein the range indicator further comprises a second set of markings on the upper hinge component that are positioned with respect to the second screw so that a marking of the second set of markings that is aligned with an end of the second screw indicates the second range of motion.

Aspect 14: The ankle prosthesis of any one of aspects 1-13, wherein the base comprises: a footplate; and a lower hinge component non-rotatably attached to the footplate.

Aspect 15: The ankle prosthesis of any one of aspects 5-14, wherein the first screw and the second screw are set screws.

Aspect 16: The ankle prosthesis of any one of aspects 2-14, wherein the first selectively extendable and retractable locking element is selectively retractable from the locking position to permit at least fifteen degrees of rotational movement of the upper hinge component in the first direction from the neutral position.

Aspect 17: The ankle prosthesis of any one of aspects 2-14 and 16, wherein the first selectively extendable and retractable locking element is selectively retractable to a fully open position in which the first selectively extendable and retractable locking element is fully retracted within the upper hinge component, and wherein a range of motion of the upper hinge component in the first rotational direction is limited by engagement between the upper hinge component and the base.

Aspect 18: The ankle prosthesis of any one of aspects 4-17, wherein the first selectively extendable and retractable locking element comprises a first platform that is pivotable about the axis and a first linear actuator coupled to, and positioned between, the base and the first platform, wherein the second selectively extendable and retractable locking element comprises a second platform that is pivotable about the axis and a second linear actuator coupled to, and positioned between, the base and the second platform, wherein the upper hinge component defines first and second stop surfaces that are positioned to engage the first and second platforms, respectively, wherein the first actuator is configured to rotationally position the first platform with respect to the first stop surface to limit movement of the upper hinge component in the first direction, and wherein the second actuator is configured to rotationally position the second platform with respect to the second stop surface to limit movement of the upper hinge component in the second rotational direction.

Aspect 19: A method of using an ankle prosthesis of any one of aspects 1-18.

Aspect 20: The method of aspect 19, wherein the method comprises: retracting the first selectively extendable and retractable locking element to disengage said other of the base and the upper hinge component; selectively rotating the upper hinge component in the first rotational direction; and advancing the first selectively extendable and retractable locking element to engage said other of the base and the upper hinge component to lock the upper hinge component in a desired rotational orientation.

Aspect 21: The method of aspect 19, wherein the method comprises: retracting the first and second selectively extendable and retractable locking element to disengage said other of the base and the upper hinge component; selectively rotating the upper hinge component in one or more of the first and second rotational directions; and advancing the first and second selectively extendable and retractable locking element to engage said other of the base and the upper hinge component to lock the upper hinge component in a desired rotational orientation.

Although the foregoing invention has been described in some detail by way of illustration and example for purposes of clarity of understanding, certain changes and modifications may be practiced within the scope of the appended claims.

What is claimed is:

1. An ankle prosthesis comprising:
   a base;
   an upper hinge component that is pivotably attached to the base about an axis;
   a first biasing element that is configured to bias the upper hinge component in a first rotational direction and toward a neutral position;
   a second biasing element that is configured to bias the upper hinge component in a second rotational direction that is opposite the first rotational direction and toward the neutral position; and
   a first selectively extendable and retractable locking element that is selectively extendable to a locking position, wherein the first selectively extendable and retractable locking element extends from one of the base and the upper hinge component and, when the upper hinge component is in the neutral position and the first selectively extendable and retractable locking element is in the locking position, the first selectively extendable and retractable locking element engages the other of the base and the upper hinge component.

2. The ankle prosthesis of claim 1, wherein the first selectively extendable and retractable locking element is selectively retractable from the locking position to permit movement of the upper hinge component in the first rotational direction from the neutral position.

3. The ankle prosthesis of claim 2, further comprising a second selectively extendable and retractable locking element that is selectively extendable to a locking position, wherein the second selectively extendable and retractable locking element extends from one of the base and the upper hinge component and, when the upper hinge component is in the neutral position and the second selectively extendable and retractable locking element is in the locking position, the second selectively extendable and retractable locking element engages the other of the base and the upper hinge component.

4. The ankle prosthesis of claim 3, wherein the second selectively extendable and retractable locking element is selectively retractable from the locking position to permit movement of the upper hinge component in the second rotational direction from the neutral position.

5. The ankle prosthesis of claim 4, wherein the upper hinge component defines a first threaded hole and a second threaded hole, wherein the first selectively extendable and retractable locking element comprises a first screw disposed within the first threaded hole, wherein the second selectively extendable and retractable locking element comprises a second screw disposed in the second threaded hole, wherein the base defines a first stop surface and a second stop surface, wherein the first screw is configured for advancement along the threaded hole to engage the first stop surface after a first select rotational displacement between the upper hinge component and the base in the first rotational direction to thereby limit a first range of motion that the upper hinge component can pivot with respect to the base in the first rotational direction from the neutral position, wherein the second screw is configured for advancement along the threaded hole to engage the second stop surface after a second select rotational displacement between the upper hinge component and the base in the second rotational direction to thereby limit a second range of motion that the upper hinge component can pivot with respect to the base in the second rotational direction from the neutral position.

6. The ankle prosthesis of claim 4, wherein the first and second selectively extendable and retractable locking elements are on opposite sides of a vertical plane that includes the axis.

7. The ankle prosthesis of claim 5, further comprising a range indicator that is configured to indicate the first range of motion and the second range of motion respectively allowed by each of the first and second selectively extendable and retractable locking elements.

8. The ankle prosthesis of claim 7, further comprising an adjustment wrench, wherein the range indicator includes markings on the adjustment wrench, wherein the markings are positioned so that when the adjustment wrench is inserted into one of the first screw and the second screw, the markings that are visible on the adjustment wrench indicate a respective range of motion allowed by said one of the first screw and the second screw.

9. The ankle prosthesis of claim 7, wherein the range indicator comprises a first window along the first threaded hole, wherein the first window is configured to show a position of an end of the first screw, and wherein the range indicator further comprises markings that indicate the first range of motion based on a relationship between the markings and the position of the end of the first screw.

10. The ankle prosthesis of claim 7, wherein the range indicator comprises a gauge comprising a plurality of markers on the upper hinge component and an indicator component that is attached to the first screw and pivotable about the axis, wherein the indicator component further comprises a pointer that rotates as the first screw moves to indicate the first range of motion on the gauge.

11. The ankle prosthesis of claim 7, wherein the range indicator comprises a spring-loaded ball attached to the first screw, wherein the upper hinge component defines at least one cavity that is sized and positioned to receive the ball.

12. The ankle prosthesis of claim 7, wherein the range indicator comprises a first set of markings on the upper hinge component that are positioned with respect to the first screw so that a marking of the first set of markings that is aligned with an end of the first screw indicates the first range of motion.

13. The ankle prosthesis of claim 12, wherein the range indicator further comprises a second set of markings on the upper hinge component that are positioned with respect to the second screw so that a marking of the second set of markings that is aligned with an end of the second screw indicates the second range of motion.

14. The ankle prosthesis of claim 1, wherein the base comprises:
a footplate; and
a lower hinge component non-rotatably attached to the footplate.

15. The ankle prosthesis of claim 5, wherein the first screw and the second screw are set screws.

16. The ankle prosthesis of claim 2, wherein the first selectively extendable and retractable locking element is selectively retractable from the locking position to permit at least fifteen degrees of rotational movement of the upper hinge component in the first direction from the neutral position.

17. The ankle prosthesis of claim 2, wherein the first selectively extendable and retractable locking element is selectively retractable to a fully open position in which the first selectively extendable and retractable locking element is fully retracted within the upper hinge component, and wherein a range of motion of the upper hinge component in the first rotational direction is limited by engagement between the upper hinge component and the base.

18. The ankle prosthesis of claim 4, wherein the first selectively extendable and retractable locking element comprises a first platform that is pivotable about the axis and a first linear actuator coupled to, and positioned between, the base and the first platform,
wherein the second selectively extendable and retractable locking element comprises a second platform that is pivotable about the axis and a second linear actuator coupled to, and positioned between, the base and the second platform,
wherein the upper hinge component defines first and second stop surfaces that are positioned to engage the first and second platforms, respectively,
wherein the first actuator is configured to rotationally position the first platform with respect to the first stop surface to limit movement of the upper hinge component in the first direction, and
wherein the second actuator is configured to rotationally position the second platform with respect to the second stop surface to limit movement of the upper hinge component in the second rotational direction.

* * * * *